(12) United States Patent
Strölin

(10) Patent No.: US 10,653,494 B2
(45) Date of Patent: May 19, 2020

(54) HANDLE DEVICE FOR A SURGICAL LIGHT WITH VOICE CONTROL, AND SURGICAL LIGHT

(71) Applicant: Karl Leibinger Medizintechnik GmbH & Co. KG, Mühlheim (DE)

(72) Inventor: Joachim Strölin, Rietheim (DE)

(73) Assignee: Karl Leibinger Medizintechnik GMBH & CO. KG, Mühlheim (DE)

(*) Notice: Subject to any disclaimer, the term of this patent is extended or adjusted under 35 U.S.C. 154(b) by 128 days.

(21) Appl. No.: 15/879,866

(22) Filed: Jan. 25, 2018

(65) Prior Publication Data

US 2018/0147020 A1 May 31, 2018

Related U.S. Application Data

(63) Continuation of application No. PCT/EP2016/067691, filed on Jul. 25, 2016.

(30) Foreign Application Priority Data

Aug. 13, 2015 (DE) .......................... 10 2015 113 338

(51) Int. Cl.
*A61B 90/30* (2016.01)
*F21V 21/40* (2006.01)
(Continued)

(52) U.S. Cl.
CPC .............. *A61B 90/30* (2016.02); *F21V 21/30* (2013.01); *F21V 21/40* (2013.01); *G10L 15/26* (2013.01); *A61B 90/361* (2016.02); *A61B 2017/00203* (2013.01); *A61B 2017/00907* (2013.01); *A61B 2090/061* (2016.02); *A61B 2090/308* (2016.02); *A61B 2090/309* (2016.02); *F21V 23/0471* (2013.01); *F21W 2131/205* (2013.01)

(58) Field of Classification Search
CPC ...... A61B 2560/0493; A61B 2090/308; A61B 90/30; F21V 21/40; F21V 21/403
See application file for complete search history.

(56) References Cited

U.S. PATENT DOCUMENTS

| 5,803,905 A | 9/1998 | Allred et al. |
| 6,160,582 A | 12/2000 | Hill |
(Continued)

FOREIGN PATENT DOCUMENTS

| DE | 19803494 | 8/1999 |
| DE | 102010034562 | 2/2012 |
(Continued)

OTHER PUBLICATIONS

Canadian Office Action dated Mar. 11, 2019 from Canadian Application No. 2,994,594.
(Continued)

*Primary Examiner* — Sean P Gramling
(74) *Attorney, Agent, or Firm* — Beyer Law Group LLP

(57) ABSTRACT

The invention relates to a handle device for a surgical light, which comprises a handle element, prepared for attachment to a receiving body of the surgical light and forming a handle surface in an exterior region. A voice control module that has at least one acoustic sensor is detachably connected to the handle element. The invention further relates to a surgical light having said handle device.

12 Claims, 8 Drawing Sheets

Figure 1:
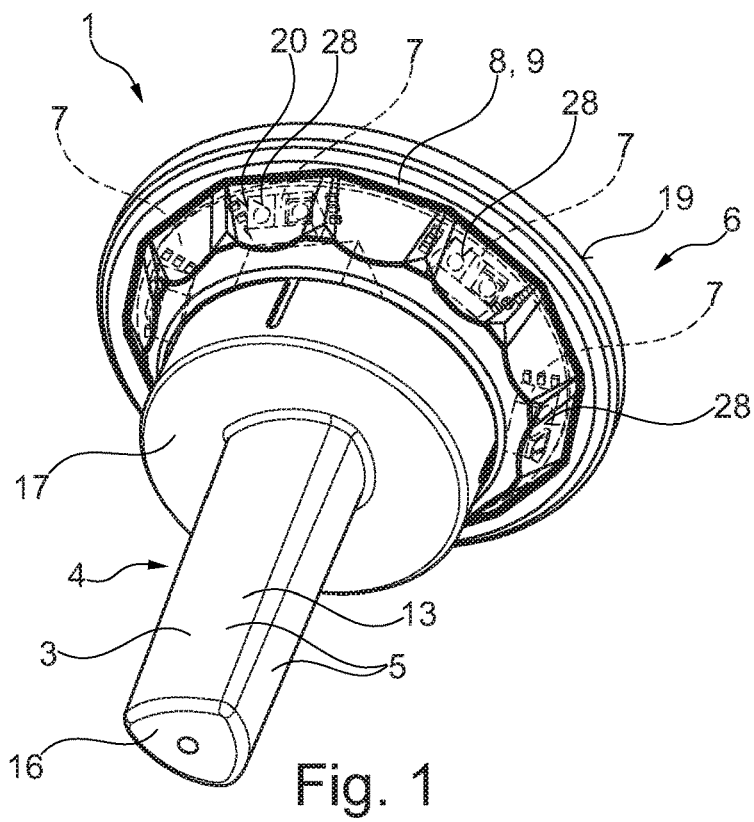

(51) Int. Cl.
  *F21V 21/30* (2006.01)
  *G10L 15/26* (2006.01)
  *A61B 17/00* (2006.01)
  *A61B 90/00* (2016.01)
  *F21V 23/04* (2006.01)
  *F21W 131/205* (2006.01)

(56) References Cited

U.S. PATENT DOCUMENTS

| | | | |
|---|---|---|---|
| 2006/0008787 A1* | 1/2006 | Hayman | A61C 19/004 434/263 |
| 2011/0124961 A1* | 5/2011 | Zimmon | A61B 1/00002 600/104 |
| 2012/0043915 A1 | 2/2012 | Rohwedder et al. | |
| 2012/0075832 A1 | 3/2012 | Schmid et al. | |
| 2013/0113909 A1 | 5/2013 | DeLand | |
| 2013/0113945 A1 | 5/2013 | Tockweiler | |
| 2013/0128223 A1* | 5/2013 | Wood | A61B 5/0077 351/206 |
| 2016/0230974 A1* | 8/2016 | Timoszyk | A61B 90/30 |

FOREIGN PATENT DOCUMENTS

| | | |
|---|---|---|
| EP | 2 590 427 | 8/1917 |
| EP | 0 933 973 | 8/1999 |
| WO | WO 2013/173258 | 11/2013 |
| WO | WO 2015/010757 | 1/2015 |

OTHER PUBLICATIONS

International Search Report and Written Opinion dated Oct. 11, 2016 from International Application No. PCT/EP2016/067691.
German Office Action dated May 19, 2016 from German Application No. 10 2015 113 338.5.
ILED 7 Brochure, "Intelligence in the Form of Light", Trumpf Medical, published in 2014, prior to Aug. 2015.
TruLight 5000 Surgical Light Brochure, www.trumpfmedical.com/en/trulight5000, Trumpf Medical, Nov. 6, 2016.
PowerLED, "The $2^{nd}$ Generation is Here!" Brochure, Maquet Medical Systems, www.maquetusa.com, Jan. 2013.

* cited by examiner

HANDLE DEVICE FOR A SURGICAL LIGHT WITH VOICE CONTROL, AND SURGICAL LIGHT

This application is a Continuation of International Application No. PCT/EP2016/067691, filed on Jul. 25, 2016, which claims priority to German Application No. 10 2015 113 338.5, filed on Aug. 13, 2015, both of which are incorporated herein by reference in their entirety.

The invention relates to a handle device for a surgical light which comprises a handle element (also referred to as handle or simply as grip) prepared for attachment to a receiving body of the surgical light and forming a handle surface in an exterior region. The invention also relates to a surgical light having said handle device.

It has been generally known so far from prior art to provide operating devices which are arranged in the surgical light. Voice controls may also be connected to said operating devices, which facilitates control of the surgical light by means of voice input.

It has turned out to be a drawback, however, that the operating devices frequently have a relatively complex design and consequently are relatively expensive to manufacture. In addition, along with the voice control mostly microphones that are relatively difficult to handle, for example in the form of headsets, are realized which are difficult to fasten to the operating surgeon wearing sterile clothes or may even obstruct the operating surgeon performing an operation.

Hence it is the object of the present invention to eliminate said drawbacks known from the state of the art and to enable voice control for a surgical light which, on the one hand, permits inexpensive manufacture of the surgical light and, on the other hand, is intended to hardly obstruct the operating surgeon in his/her operating activities.

In accordance with the invention, this is achieved by the fact that a handle device is provided, wherein a voice control module that has at least one acoustic sensor is detachably connected to the handle element thereof.

The design of such voice control module ensures that during operation the operating surgeon can always freely control both the surgical light itself and various means coupled to the surgical light, e.g. camera pictures, in a contactless manner by mere voice commands/inputs. The arrangement of the voice control module in the handle device moreover automatically ensures that during operation the operating surgeon is within reach of the acoustic sensor, as he/she is usually standing in the vicinity of the surgical light anyway. This further ensures that the operating surgeon's voice inputs can also be correctly recognized by the voice control module with relatively high certainty. Furthermore, the modular structure allows, when the final user of a surgical light previously configured without any voice control module intends to change to a surgical light including a voice control module, to simply replace the existing handle device with the handle device of the type according to the invention. Therefore, no completely new surgical light has to be purchased, which further improves the range of application of the handle device. Since the known handle devices usually are exchangeable anyway so as to remove them for sterilization, in this way also the expenditure for retro-fitting of the surgical light is especially low.

Further advantageous embodiments are claimed in the subclaims and will be described in detail in the following.

It is further advantageous when the voice control module includes a housing in which the at least one acoustic sensor is received/arranged/fastened. The acoustic sensor used may be a microphone. In this way a preferably robust design of the voice control module is formed and the acoustic sensor is largely protected against the environment.

In addition, it is also advantageous when plural acoustic sensors preferably oriented in different spatial directions are present in the voice control module. This allows for an even more sensitive voice input.

In this context, it is of further advantage when the housing includes/forms a disk-shaped hollow portion within which the at least one acoustic sensor is arranged/fastened. In this way, the voice control module has an especially compact design and requires as little space as possible.

When the housing is configured to be transmissive to a sound signal to be detected by the at least one distance sensor (i.e. sound-transmissive) in the area of the at least one acoustic sensor, the at least one acoustic sensor is especially advantageously accommodated in the housing so as to be protected against the environment.

It is also useful when the voice control module includes a handle receiving portion detachably connected to the handle element. This allows to replace a handle element rendered unsterile before with a new/sterile handle element in an especially simple manner without having to remove the voice control module as well.

In this context, it is also advantageous when the handle receiving portion forms a receiving pivot onto which a sleeve portion of the handle element including the handle surface is attached/slipped on, i.e. positively applied in at least one operating state of the handle device. In this way, an especially stable holder of the handle element relative to the voice control module is realized.

In this context, it is of further advantage when the handle element is positively and/or non-positively connected to the voice control module in at least one operating state, as thus the handle element can be replaced especially quickly.

Moreover, it is advantageous when the voice control module includes a computer unit (also referred to as computing unit) which is electrically connected to the at least one acoustic sensor and generates control signals for controlling the surgical light in response to the measuring data determined by means of the at least one acoustic sensor. This helps to realize a particularly direct electric connection/supply of the at least one acoustic sensor. During operation, the surgical light then may be controlled in response to said control signals, for example, directly in such way that lamp elements/individual lamps of the surgical light can be dimmed or deactivated.

Further preferred, the computer unit of the voice control module is connected to a central control unit of the surgical light during operation so that the individual lamps of the surgical light can be individually controlled/actuated. Also, numerous further functions may be realized by means of the voice control module and, for example, control signals can be generated for varying the height adjustment or the inclination of the surgical light. This allows to avoid direct contact of the operating surgeon with the surgical light during operation.

It is also advantageous when the voice control module (preferably the computer unit) is connected (electrically/cable-bound or wirelessly) to an image-recording device. This renders also an image-recording device especially easily controllable. Further preferred, said image-recording device is equally integrated in the handle device (preferably in a separate module or in the voice control module). Thus, especially space can be significantly saved.

Moreover, it is advantageous when at least one distance sensor designed for detecting a position of an object is included in the voice control module. This enables a brightness regulation to be simultaneously realized, apart from the control via voice input, by means of distance sensors.

If moreover the at least one distance sensor is an infrared sensor, the voice control module is equipped with proven measuring sensors which permit even more inexpensive manufacture of the handle device.

In this context, it is also useful to electronically connect the at least one distance sensor to the computer unit. This helps to further facilitate the design of the voice control module.

In addition, the invention comprises a surgical light including a handle device according to at least one of the afore-mentioned embodiments, wherein the handle device is at least partially detachably connected to a receiving body of the surgical light, thus allowing to realize especially simple suitability for sterilization of the handle device.

It is also advantageous in this context when the voice control module is detachably attached to the receiving body. In that case, the voice control module may be quickly removed from the surgical light after preceding mounting, if needed. Thus, the surgical light can be equipped especially individually.

When a computing unit of the voice control module is wire-connected/cable-connected/electrically connected to a central control unit of the surgical light, control signals can be transmitted from the voice control module directly to the surgical light, thus enabling the surgical light to individually and directly adjust its individual lamps (especially regarding their brightness/illumination intensity). The control of the surgical light is thus realized as directly as possible.

Instead, it is also useful when the computer unit of the voice control module is connected to a central control unit of the surgical light by means of wireless data communication (preferably via "Bluetooth" data communication). This renders the design especially simple.

In accordance with the invention, thus a handle device for a surgical light is realized which can be controlled via speech without having to be touched. Therefore, the operating surgeon need not touch the surgical light, thus avoiding any risk of getting unsterile during operation. The advantage of accommodating the voice control (the voice control module) or parts thereof in the central handle group/handle device is that for this function it is the ideal place, as the user is located most closely for inputting a command. The operating surgeon is almost constantly standing exactly beneath the surgical light and therefore is at a distance of only few cm or maximally 0.5 m from the central handle/the handle device.

The prior art voice controls frequently are expensive, wherefrom, when they are fixedly mounted in the receiving body, a high purchase price is resulting. According to the invention, the voice control or parts thereof is/are provided in the central handle unit of the surgical light. Said central handle unit is easy to replace. So, a surgical light can be retro-fitted very easily and quickly with voice control. In a first variant, different handle groups are provided, one including voice control and one without voice control, which then can be easily exchanged. In a second variant, the voice control is mounted between the handle group and the receiving body as an intermediate ring. When arranging the voice module/voice control module in/at the central handle/ the central handle device, also the microphone/acoustic sensor and the loudspeaker of the voice module are arranged within the central handle. The voice control/the voice control module could alternatively communicate also directly with a mounted camera of an image-recording device without the detour via the surgical light electronics (i.e. the central control unit). A video recording function of the camera, e.g. on a memory card directly inside the handle group would also be imaginable. The recording is preferably started/stopped via voice control. Also, a voice memo recording via voice control directly on the integrated memory card would be imaginable.

It is further imaginable that the voice control corresponds to a hands-free set which may also be used for phone calls. The voice module establishes communication with any mobile phone/cell phone (operating surgeon) (e.g. via Bluetooth). This allows the user to use his/her contacts and to make a phone call and simultaneously or staggered in time to control the surgical light by voice control.

In this context, it is useful to employ an acoustic output unit such as a loudspeaker. Due to the use of a loudspeaker conventional music may be played. It is of advantage when the loudspeaker is positioned directly behind a wipeable membrane.

The control of the surgical light may be used, additionally or alternatively, for messaging, making telephone calls, controlling video cameras and/or photo cameras and, resp., for playing music.

Figure 2:
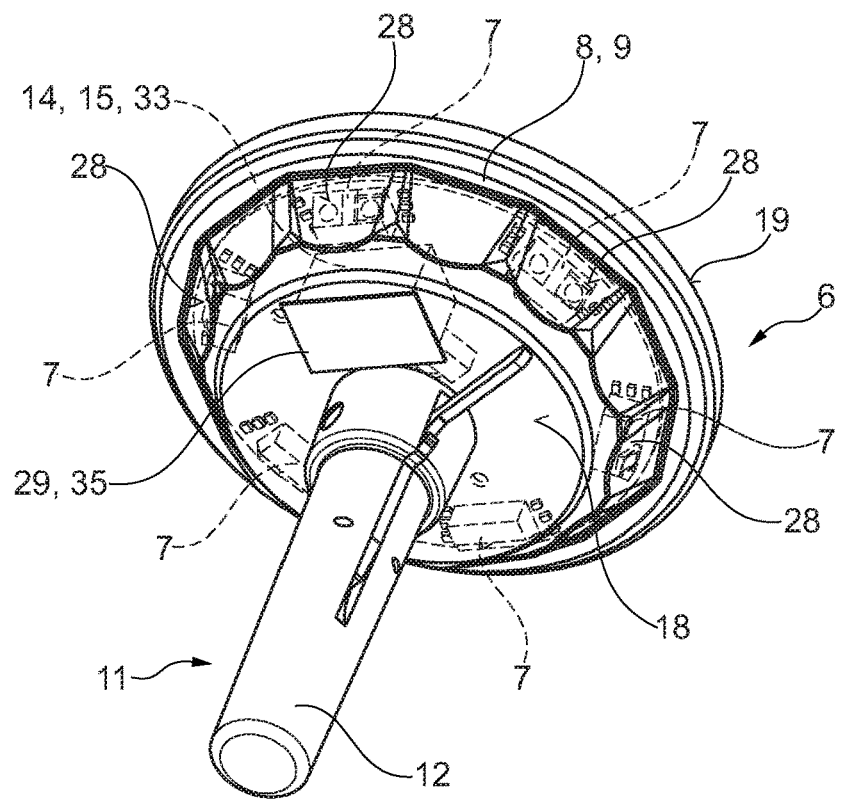
Figure 3:
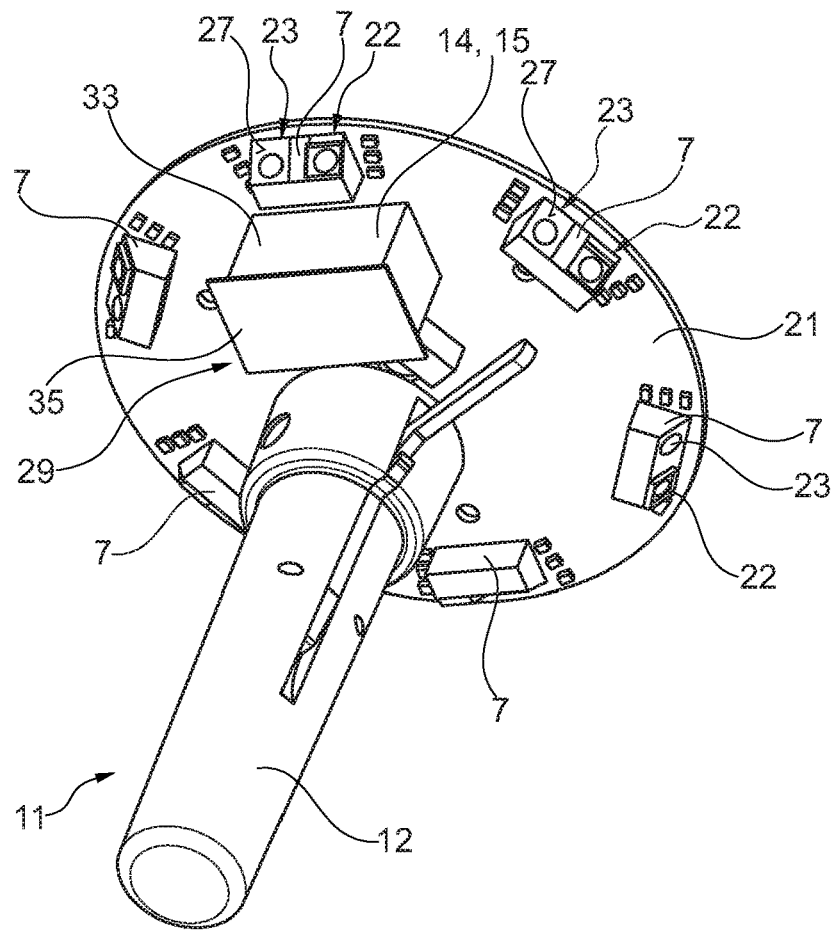
Figure 4:
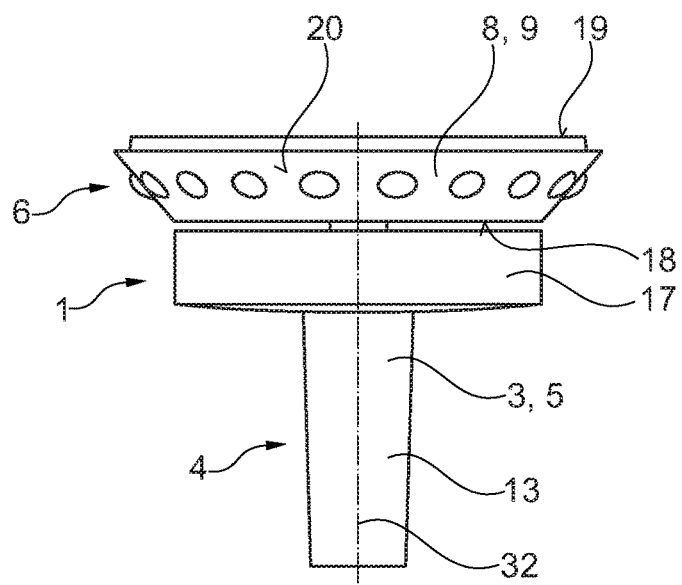
Figure 5:
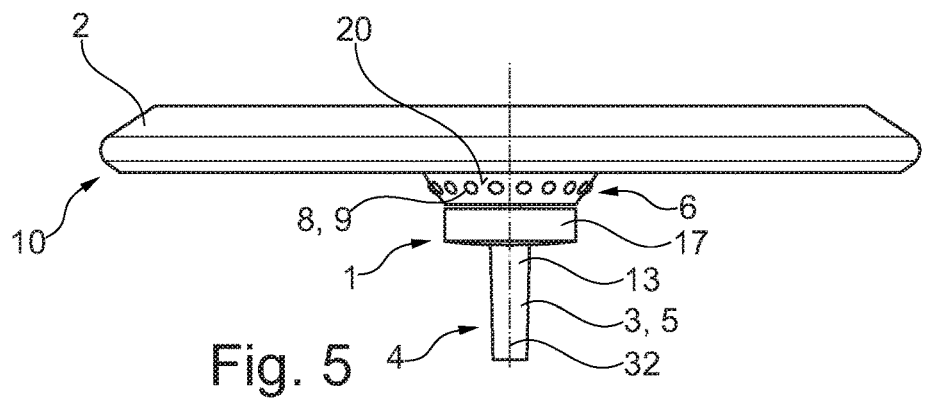
Figure 6:
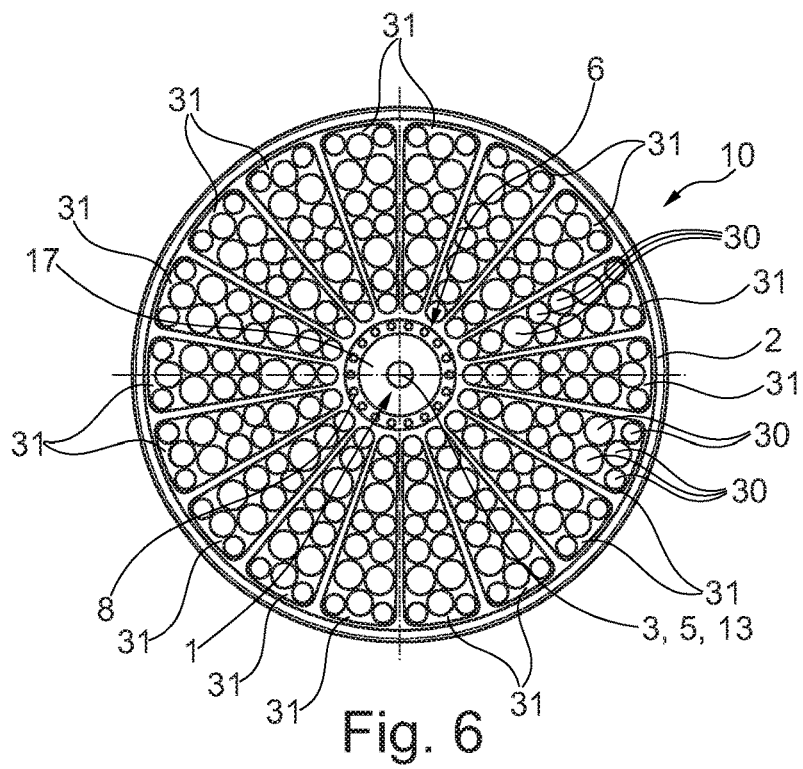
Figure 7:
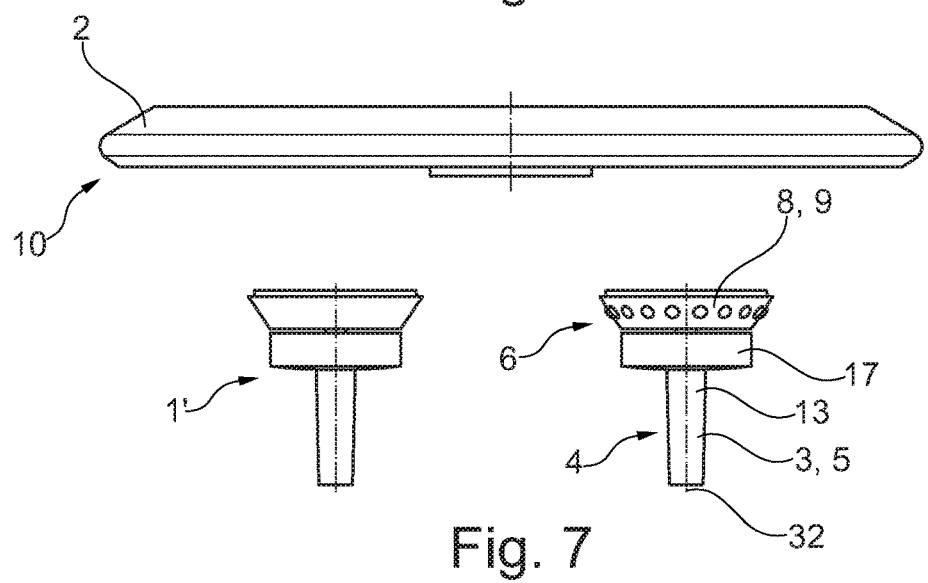
Figure 8:
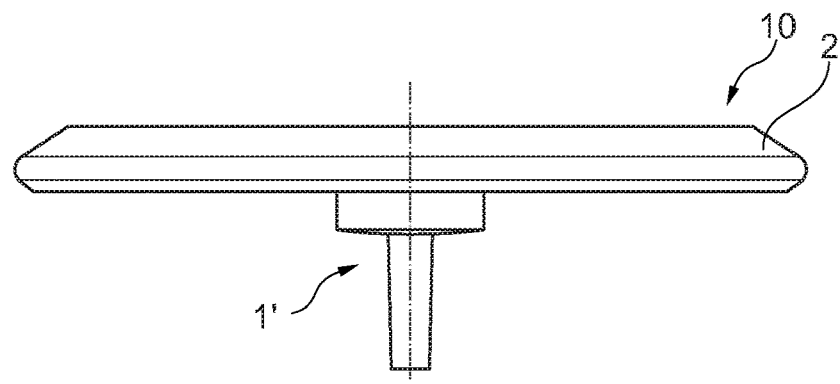
Figure 9:
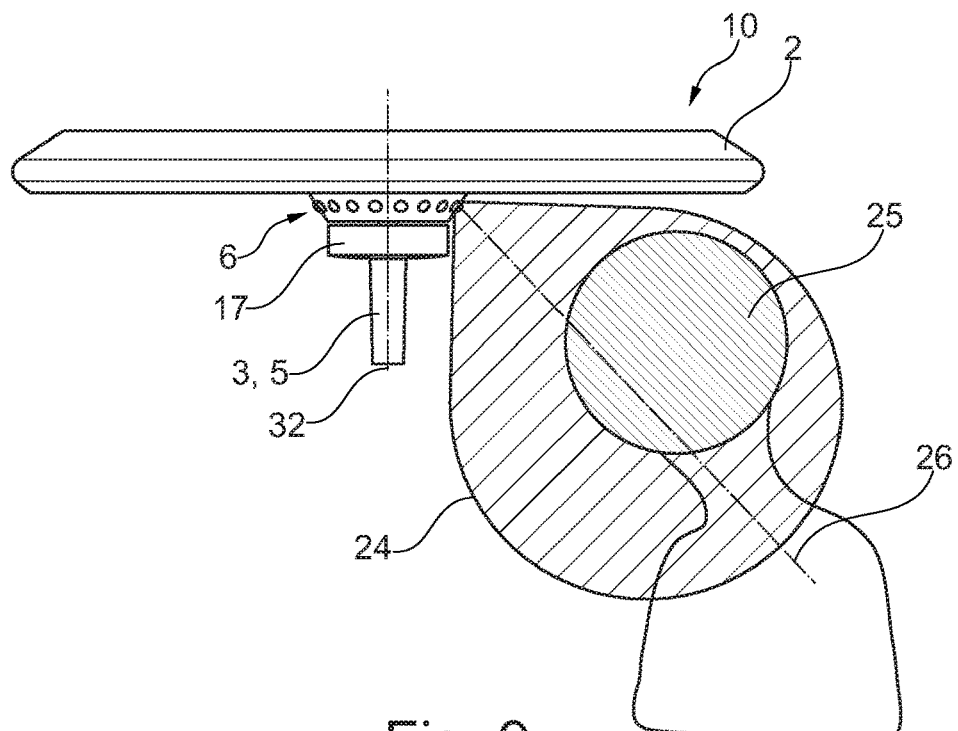
Figure 10:
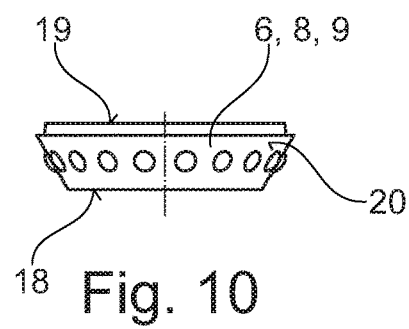
Figure 11:
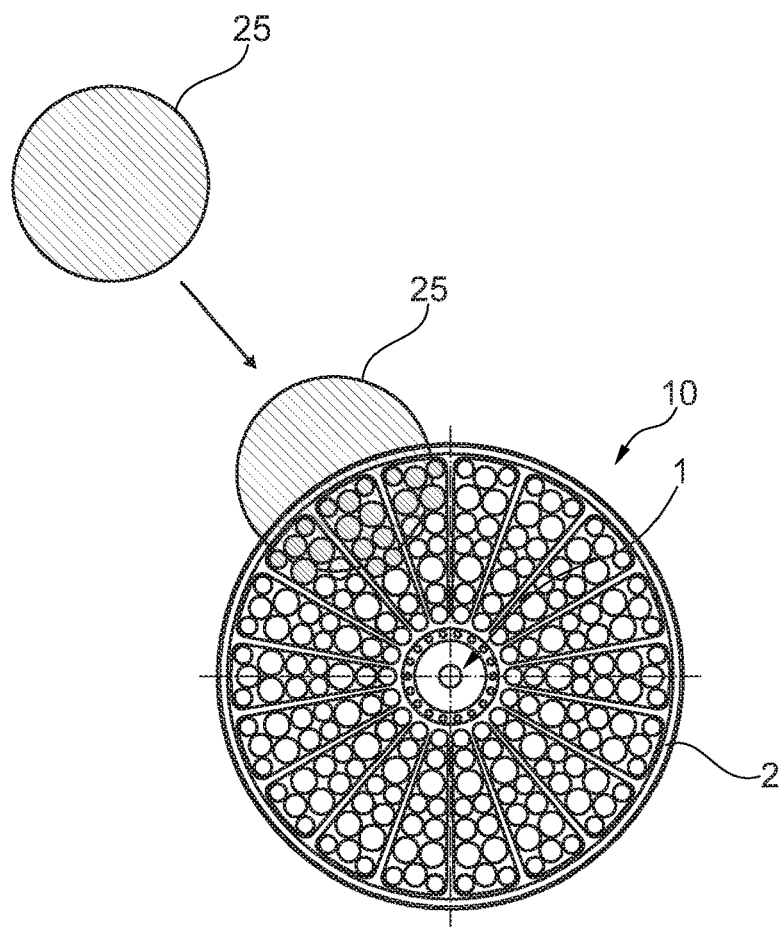
Figure 12:
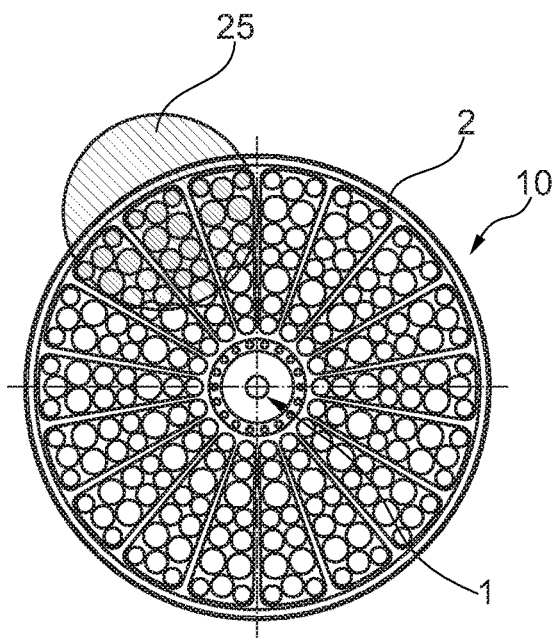
Figure 13:
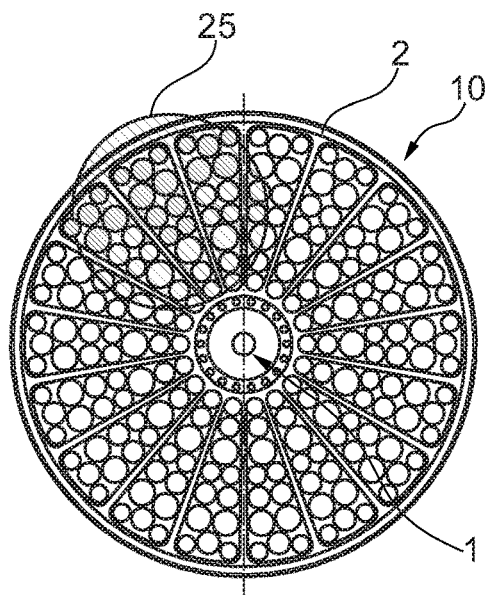
Figure 14:
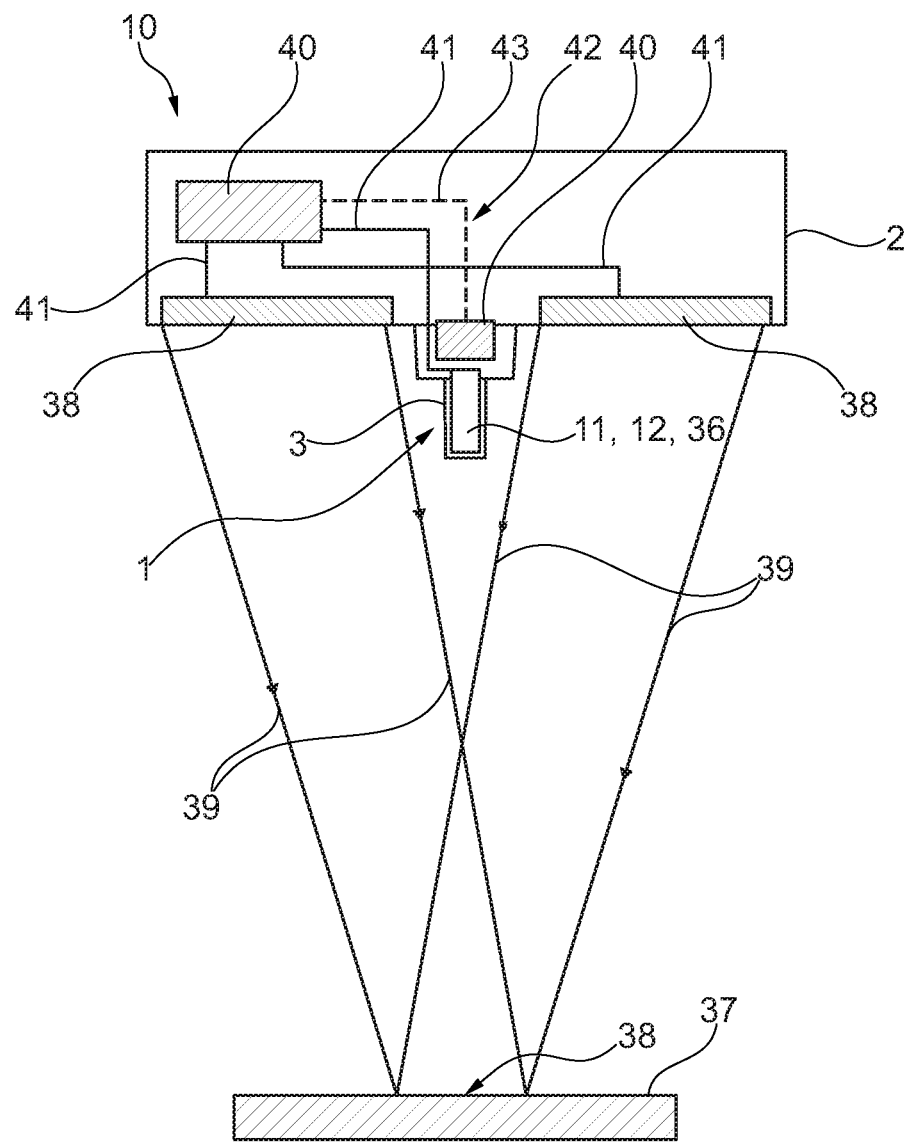
Figure 15:
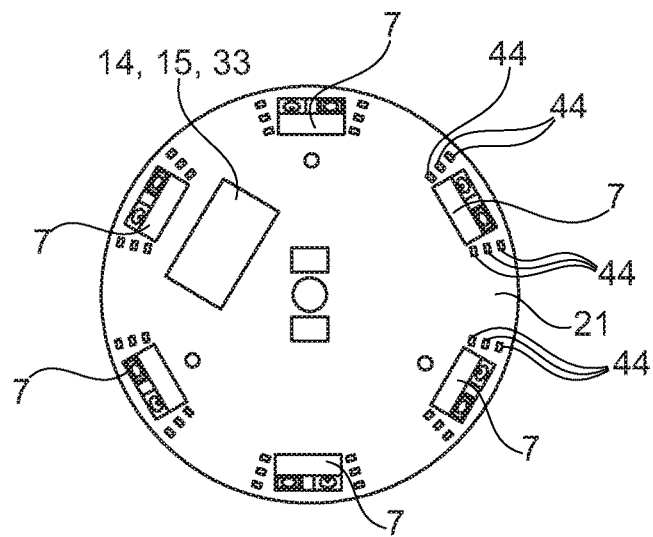
Figure 16:
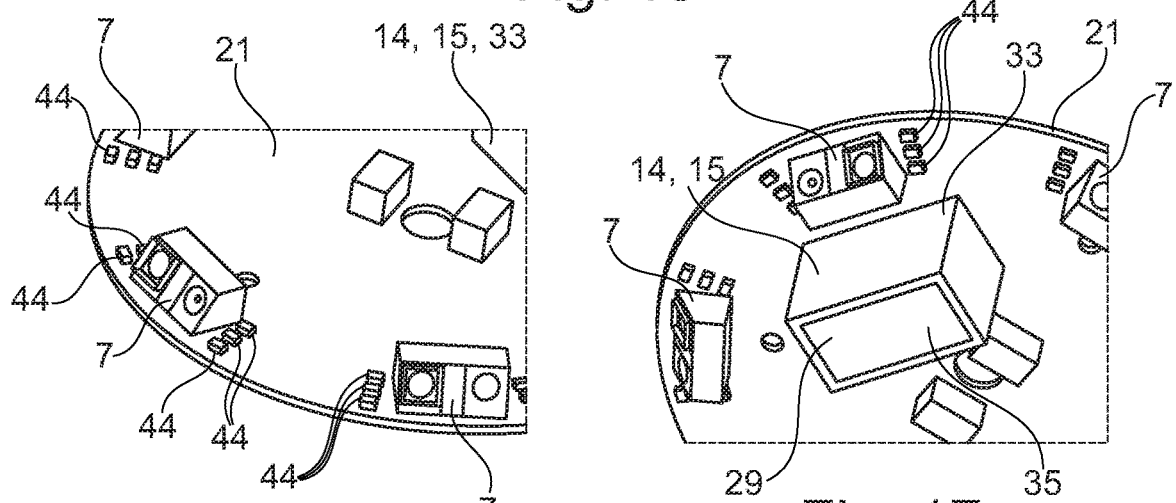
Figure 17:
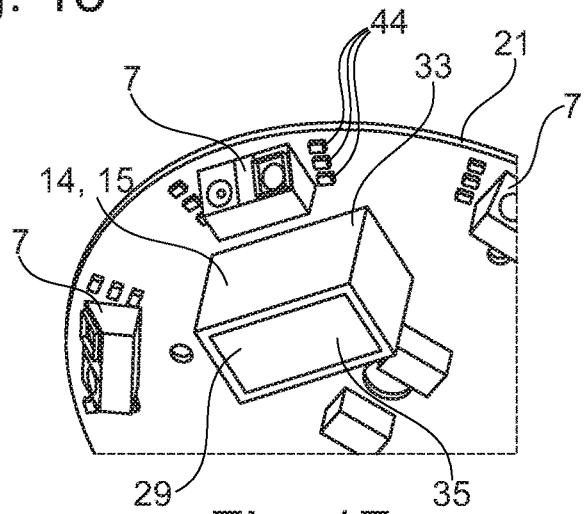
Figure 18:
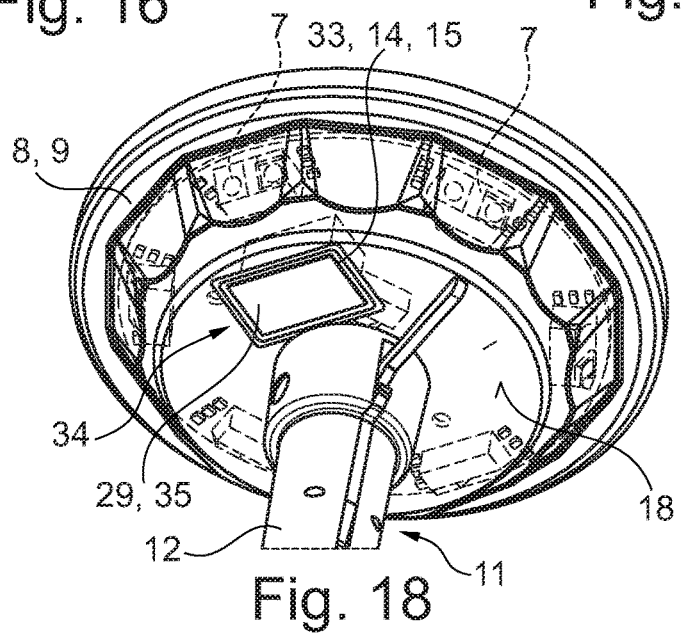
Figure 19:
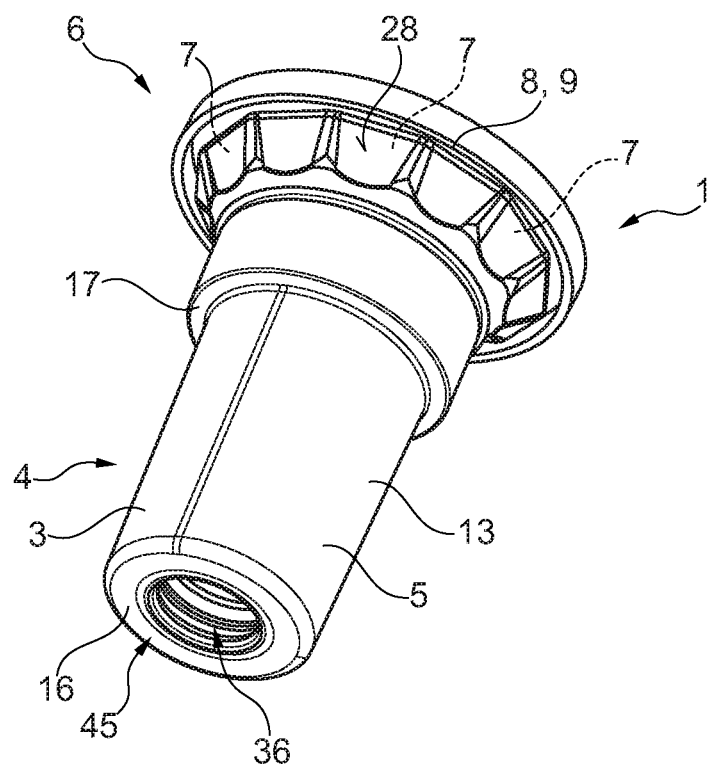
Figure 20:
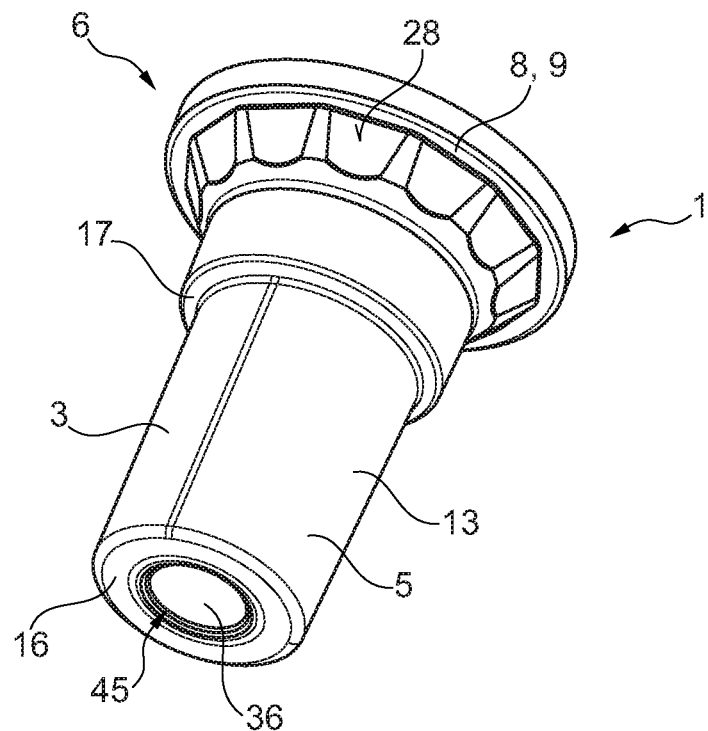

Hereinafter the invention shall be described in detail by way of Figures in which context also various embodiments are described, wherein:

FIG. 1 shows an isometric representation of a handle device according to the invention in accordance with a first embodiment in which a handle element is tightly connected to a voice control module, FIG. 2 shows an isometric representation of the handle device of FIG. 1, wherein now merely the voice control module is shown and the handle element is removed from a receiving pivot of the voice control module, and wherein an electronic housing enclosing an acoustic sensor is evident behind the outer wall of the housing of the voice control module shown to be slightly transparent, FIG. 3 shows an isometric representation of part of the voice control module according to FIG. 2, wherein the interior of the housing in which the printed circuit board receiving the acoustic sensor is arranged is evident, FIG. 4 shows a schematic side view of the handle device according to FIG. 1, wherein the arrangement between the voice control module and the handle element is evident, FIG. 5 shows a side view of a surgical light according to the invention in accordance with a first advantageous embodiment, wherein the handle device is schematically shown as in FIG. 4 already and is fastened to a receiving body of the surgical light, FIG. 6 shows a bottom view of the surgical light shown in FIG. 5, wherein the different lamp fields of the surgical light including a plurality of individual lamps illuminating the wound field during operation are especially clearly evident, FIG. 7 shows a schematic side view of a surgical light having two different handle devices in a dismounted state, wherein the right one of the two shown handle devices is the handle device according to the invention of FIG. 1 and, resp., FIG. 4 and the left one of the two handle devices is a handle device known from prior art, both handle devices being adapted to be fastened to the shown receiving bodies of the surgical light, FIG. 8 shows a prior art surgical light, i.e. including a handle device without the voice control module according to the invention, FIG. 9 shows a schematic side view of a surgical light according to the invention of FIGS. 5 and 6, wherein an active area of a distance sensor of the voice control module produced during operation is especially clearly evident, and wherein an object, viz. a head of a person, is present within the active area of the distance sensor, FIG. 10 shows a schematic side view of a voice control module for a handle device according to an advantageous further embodiment, wherein the voice control module now is ring-shaped and includes no receiving pivot, FIG. 11 shows a schematic bottom view of the surgical light according to the invention, wherein, as in FIG. 9, within the reach of the voice control module and, resp., the distance sensors thereof a round object as marked by the arrow is moved into the light beam bundles of individual lamp fields, whereupon the individual lamps of the lamp fields shown to be dark are automatically dimmed due to the detected position by means of at least one distance sensor with the aid of a computer unit, FIG. 12 shows a bottom view of the surgical light according to FIG. 11, wherein the object now is moved further toward the central handle/central handle device and, as compared to FIG. 11, further individual lamps of the lamp fields are deactivated, FIG. 13 in turn shows a bottom view of the surgical light according to FIGS. 11 and 12, wherein, as compared to FIG. 12, the object is moved even further toward the center, i.e. toward the handle device and then even more individual lamps of the surgical light are dimmed/deactivated, FIG. 14 shows a schematic side view of a surgical light according to the invention comprising a handle device according to the invention in accordance with another advantageous embodiment, wherein an image-recording device is integrated now inside the handle device, FIG. 15 shows an inner side, i.e. a side facing the interior of the hollow portion, of the printed circuit board of the voice control module already shown in FIG. 3, FIG. 16 shows an isometric detailed view of the printed circuit board of FIG. 15 in the area of two adjacent distance sensors, wherein the display lamps thereof are clearly evident, FIG. 17 shows an isometric detailed view of a printed circuit board of a handle device according to a further advantageous embodiment, wherein the voice recognition unit thereof is clearly evident, FIG. 18 shows an isometric representation of a handle device according to another advantageous embodiment into which the printed circuit board according to FIG. 17 is inserted, FIG. 19 shows an isometric representation of a handle device according to another advantageous embodiment in which an image-recording device is integrated, and FIG. 20 shows an isometric representation of the handle device according to FIG. 19, wherein the housing of the voice control module is no longer shown to be transparent.

The Figures are merely schematic and serve exclusively for the comprehension of the invention. Like elements are provided with like reference numerals. The features of the different embodiments may as well be freely combined.

In FIG. 1, at first a handle device 1 according to the invention in accordance with an advantageous first embodiment is clearly evident. The handle device 1 is prepared for assembly/for temporary attachment to a surgical light 10 described in detail hereinafter in FIGS. 5 to 9 and 11 to 13. Thus, the invention does not only relate to the handle device 1 itself but also to a surgical light 10 comprising said handle device 1.

The handle device 1 includes a handle element 3 prepared for attachment to a receiving body 2 of the surgical light 10, which handle element 3 is also simply referred to as handle. The handle element 3 consequently is dimensioned so that it can be gripped by a hand of a person such as an operating surgeon so as to move the surgical light in an operating state of the handle device 1 in which it is tightly connected to the receiving body 2 of the surgical light 10 into the desired position. The surgical light 10 hereinafter (e.g. in connection with FIGS. 5 and 6) described in detail further includes a support structure not shown here for reasons of clarity which is connected to the receiving body 2 and by which the receiving body 2 can be freely positioned. Also, the support structure includes an electrically operable drive not shown here in detail for reasons of clarity which is electrically connected to a central control unit of the surgical light.

In an exterior region 4 of the handle element 3 a handle surface 5 is formed which the operating surgeon touches during operation for changing the position of the surgical light 10. The handle element 3 per se includes a rod-type hollow sleeve portion 13 extending in the longitudinal direction. Directly on the outer peripheral side/outer shell side thereof the handle surface 5 is formed. The handle element 3 is configured in its exterior region 4 in such a way that it has an as smooth surface/handle surface 5 as possible which can be easily sterilized. That is to say, the roughness of the handle surface 5 is selected so that cleaning with subsequent sterilization can be easily carried out and dirt particles are prevented from being trapped.

The sleeve portion 13 includes a cover 16 protecting/closing off the interior of the sleeve portion 13 toward the environment at an end side facing away from the receiving body 2 during operation. The cover 16 therefore forms a first axial end region of the sleeve portion 13 of the handle element 3. By a second end region opposite to the first end region the sleeve portion 13 merges into a disk-shaped broadening portion 17. The broadening portion 17 and the sleeve portion 13 are formed integrally from one material, i.e. are connected to each other in one piece.

In turn, a voice control module 6 according to the invention is connected to the handle element 3. The voice control element 6 is detachably connected to the handle element 3. The voice control module 6 is connected by form-locking and friction-locking to the handle element 3. In turn, the voice control module 6, which is evident in total from FIG. 2 in a state dismounted from the handle element 3, includes a housing 8. The housing 8 again has a disk-shaped hollow portion 9 and, resp., is formed by said disk-shaped hollow portion 9. The disk-shaped hollow portion 9 is sealed toward the environment. On the one hand, the hollow portion 9 is formed by two walls spaced apart from each other—a front wall 18 and a rear wall 19. On the other hand, the hollow portion 9 includes an annularly extending sidewall 20 connecting the front wall 18 to the rear wall 19. The front wall 18 is the flatly extending wall of the hollow portion 9 which during operation faces the handle element 3, whereas the rear wall 19 of the housing is the flatly extending wall of the hollow portion 9 which during operation is facing away from the handle element 3.

Furthermore, the voice control module 6 includes, apart from the housing 8, a handle receiving portion 11 tightly connected to the housing 8/the hollow portion 9. Said handle receiving portion 11 is tightly connected to the front wall 18 of the hollow portion 9. The handle receiving portion 11 forms a receiving pivot 12 extending perpendicularly away from the front wall 18 of the hollow portion 9 extending in an imaginary extension plane. A longitudinal axis 32 of the receiving pivot 12 thus extends perpendicularly to the front wall 18 and, resp., to the extension plane.

The receiving pivot 12 is dimensioned and adapted to the sleeve portion 13 of the handle element 3 such that it can be inserted into the sleeve portion 13. In the assembled state of the handle device 1 shown in FIG. 1 said receiving pivot 12 is inserted in the sleeve portion 13 by form-fit and force-fit. Therefore, the handle element 3 is connected to the voice control module 6 by form-locking and friction-locking. As is also evident from the schematic representation according to FIG. 4, the broadening portion 17 in said assembled state is maintained at a distance from the front wall 18 in the axial direction of the receiving pivot 12 (corresponding to the axial direction of the longitudinal axis 32 and, resp., of the sleeve portion 13).

FIG. 3 finally illustrates the internal structure of the voice control module 6. For the sake of clarity, as compared to FIG. 2, in FIG. 3 the housing 8/the hollow portion 9 is omitted, which allows to especially clearly recognize the electronic unit/electronic design of the voice control module 6. On a disk-shaped printed circuit board 21 of the voice control module 6 plural distance sensors 7 are positioned next to an electronic housing 33 including/enclosing/receiving a first acoustic sensor 29. All of said distance sensors 7 have the same design and function and are illustrated in detail further below.

The electronic housing 33 is further electronically connected to a computer unit 14 disposed on the printed circuit board 21. The electronic housing 33 accommodates the computer unit 14 even in such a way that the latter is surrounded by the electronic housing 33. In this configuration, the computer unit 14 thus is integrated in the electronic housing 33. Apart from the computer unit 14, the acoustic sensor 29, also referred to as microphone, is also accommodated in the electronic housing 33. Therefore, the acoustic sensor 29 is integrated in the electronic housing 33 in the form of a voice recognition unit 15 (also referred to as voice recognition module or voice control unit). The acoustic sensor 29 is electrically connected to the computer unit 14. Thus, in a state of the handle device 1 connected to the surgical light 10 during operation, control signals in the form of acoustic signals are detected/recorded by the acoustic sensor 29 and are electrically transmitted to the computer unit 14. In this way, control commands can be transmitted to the central control unit by the computer unit 14 which is electrically connected in turn in this operating state to a central control unit of the surgical light 10 not shown here for reasons of clarity. This allows the surgical light 10 to be controlled individually by individual voice commands recorded by the acoustic sensor 29.

Apart from operating the brightness/illumination intensity of the respective individual lamps 30 of the surgical light 10, it is also possible to vary e.g. a position of the surgical light 10 by actuating an electric drive acting on the support structure of the surgical light 10 by means of said voice commands. The voice recognition unit 15 further includes a loudspeaker that is equally integrated in the electronic housing 33.

As is evident from FIG. 2, the front wall 18 of the hollow portion 9 comprises a recess adapted to the electronic housing 33 and, resp., to the acoustic sensor 29 into which an outer cover 35/membrane configured for sound transmission is inserted. In FIGS. 2 and 3 a sound-transmissive outer cover 35 of the microphone 29 projects from the electronic housing 33 toward all sides. Consequently, sound transmission is possible through the front wall 18 into the interior of the housing 8 and of the electronic housing 33 toward the acoustic sensor 29.

In another embodiment, the computing unit 14 is not cable-connected, as in this case, to the central control unit of the surgical light 10, but is wirelessly connected via Bluetooth data communication.

In this way, corresponding to the determined position of the object 25, the single lamps/individual lamps 30 of the lamp fields 31 of the surgical light 10 illuminating the object 25 can be dimmed or appropriately deactivated.

Moreover, according to the first embodiment, each of the distance sensors 7 is electronically connected to the computer unit 14 arranged on the printed circuit board 21. The distance sensors 7 are in the form of infrared sensors (also referred to as infrared distance sensors). Each distance sensor 7 has a substantially drop-shaped/balloon-shaped active area 24 within which an object 25 such as a head of the operating surgeon can be detected. For this purpose, by an infrared transmitter 22 of the distance sensor 7 infrared light is emitted which propagates in space substantially in funnel/cone shape along an imaginary directional axis 26. Apart from the infrared transmitter 22, the distance sensor 7 also includes an infrared receiver 23. The infrared receiver 23 is designed and configured so that, when an object 25 is located within the active area 24, it detects a part of the infrared light emitted before by the infrared transmitter 22 and reflected by the object 25 by measurement.

The active area 24 is especially clearly evident from FIG. 9, wherein the handle device 1 is already mounted on the surgical light 10 in this picture. The part of infrared light reflected by the object 25 therefore is supplied to the infrared receiver 23 which converts the reflected infrared light to a control signal. Depending on the distance of the object 25 from the distance sensor 7/from the infrared receiver 23, the infrared receiver 23 detects the signal at an earlier or later point in time relative to the time of transmission of the infrared light by the infrared transmitter 22. In this way, the distance between the object 25 and the handle device 1 can be easily detected. The active area 24 is consequently restricted by the shape of the emitted infrared light as well as by the reach of the infrared receiver 23. Each distance sensor 7 thus is configured for detecting/determining a position of the object 25 within an area between the lamp receiving case 2 and a wound field via the distance of the object 25 relative to the distance sensor 7 and, resp., to the voice control module 6. Due to the different sensors—acoustic sensor 29 and distance sensors 7—the voice control module 6 is also referred to as sensor module.

The distance sensors 7 are arranged on the printed circuit board 21 in such way that the active area 24 thereof with its directional axis 26 is oriented transversely/tilted relative to the longitudinal axis 32 of the receiving pivot 12, especially preferred offset against said longitudinal axis 32 by about 45°. The infrared transmitter 22 and the infrared receiver 23 are arranged/oriented in a receiving plane 27 which is oriented normal to the directional axis 26.

In this embodiment, six distance sensors 7 are arranged to be distributed substantially along a circular imaginary peripheral line around the longitudinal axis of the receiving pivot 12, wherein also different numbers of distance sensors 7, for example less or more than six, preferably seven, eight, nine or at least ten distance sensors 7, are chosen in further embodiments, however. The distance sensors 7 are arranged to be equally spaced along the imaginary peripheral line and take a substantially equal distance from the longitudinal axis 32 of the receiving pivot 12. The distance sensors 7 are arranged and oriented such that by their active areas 24 they are adapted to detect the position of an object 25 within the entire periphery, i.e. within an angular range of 360° around the longitudinal axis 32. In FIG. 15, once again the distribution of the distance sensors 7 is schematically represented, with the computer unit 14 having no microphone 29 in this view for reasons of clarity.

For indicating whether an object 25 is provided in the active area 24 of the respective distance sensor 7, plural display lights 44 for each distance sensor 7 are further arranged on the printed circuit board 21, especially clearly evident in FIG. 16. When an object 25 is provided in the active area 24 of the respective distance sensor 7, the number of illuminated/activated display lamps 44 is increased with a decreasing distance between the distance sensor 7 and the object 25. In this configuration, six display lamps 44 are present for each distance sensor 7. Each display lamp 44 is in the form of a LED. It is also possible to switch between different display lamps 44 which differ by their color depending on the distance between the distance sensor 7 and the object 25.

As is especially clearly visible also in FIGS. 1 and 2, the sidewall 20 of the housing 8 is formed to have plural cover areas 28. Each cover area 28 extends in parallel to the receiving plane 27 and thus conically between the front wall 18 and the rear wall 19. The circular front wall 18 has a smaller diameter than the equally circularly formed rear wall 19. The sidewall 20 in this configuration is made from a material which is permeable to the measuring signals of the distance sensors 7. Consequently, this sidewall 20 is transparent to infrared light. Since the conically shaped housing 8/the conically shaped hollow portion 9 as a whole is made from the same material, it is made from a material transparent to infrared light as a whole. Apart from the infrared-transparent sidewall 20, thus also the front wall 18 is transparent to infrared light. Consequently, a cover area 28 extending in parallel to the receiving plane 27 thereof is associated with each distance sensor 7, the cover area extending substantially by the same width as the respective distance sensor 7.

From FIGS. 5 and 6 especially clearly a surgical light 10 according to the invention comprising a mounted handle device 1 according to FIGS. 1 to 4 is evident. The surgical light 10 includes the lamp receiving body 2 also referred to as a base in which plural individual lamps 30 are inserted. The particular individual lamps 30 in this embodiment are combined/grouped with further individual lamps 30 to form different lamp fields 31. In this design, the surgical light 10 includes a substantially disk-shaped and housing-type lamp receiving body 2 which, in further designs, also has different configurations, however, and may also be formed from several parts, for example, i.e. from plural lamp receiving body segments. The lamp fields 31 (also referred to as lighting fields) are each functioning, controlled and designed substantially equally.

Each lamp field 31 has the same number of individual lamps 30. The individual lamps 30 of a lamp field 31 vary as to their size and/or brightness/luminous intensity/illumination intensity. The luminous color of the individual lamps 30 is also varying. Each lamp field 31 is in the form of a cake-shaped piece of the total number of individual lamps 30 extending in disk shape around the central handle device 1. Each of the individual lamps 30 comprises exclusively one LED, in further designs also plural LEDs, however. Each individual lamp 30 comprises a lens/optical lens system associated with the LED. Each of the individual lamps 30 is electrically connected to the central control unit of the surgical light 10 and can be independently regulated in response to the control signals from the central control unit, and can especially be regulated as to its luminous intensity/luminous color.

As is evident in connection with FIGS. 9 and 11 to 13, during operation of the surgical light 10 monitoring of an area illuminated by the individual lamps 30 is realized by the distance sensors 7. The individual distance sensors 7 preferably act within a reach of more than one meter, preferably of more than two meters in the direction of the directional axis 26. Thus, due to an object 25 entering the light beam/the light beam bundle of an individual lamp 30 according to FIGS. 11 to 13, the distance between the object 25 and the voice control module 6 is detected by the distance sensors 7 and then a control signal is generated by the computer unit 14, thus causing the individual lamps 30 of the lamp fields 31 concerned (i.e. the individual lamps 30 directly illuminating the object by their light beam bundles) to be dimmed or deactivated by means of the central control unit. Dimming is performed in this case depending on the height distance between the surgical light 10 and the object 25. As is clearly evident from FIGS. 11 to 13, according to FIG. 13 the lamp fields 31 can be deactivated/dimmed as a whole or the individual lamps 30 of the lamp fields 31 can be deactivated/dimmed individually, depending on the position of the object 25 relative to the handle device 1/to the distance sensor 7.

In its mounted state, the handle device 1 is fastened centrally to the lamp receiving body 2 and is thus arranged with the longitudinal axis 32 coaxially to an imaginary central axis of the lamp receiving body 2.

Moreover, also the acoustic sensor 29 has a reach of at least one meter, especially preferred of at least two meters, thus allowing acoustic sources generating a corresponding acoustic control signal, such as the object 25 itself, to be detected so as to appropriately control the surgical light 10.

In FIGS. 7 and 8, once again the advantageous design of the handle device 1 as well as the interaction with the surgical light 10 is especially clearly visible. Thus, it is easy to replace a conventional prior art handle device 1', as shown in FIG. 8 and, resp., on the left side in FIG. 7, with a handle device 1 according to the invention, as shown on the right side in FIG. 7, by removing the detachable part of the previous handle device 1' from the surgical light 10 and fastening the handle device 1 according to the invention to the lamp receiving body 2. For this purpose, the voice control module 6 forms a detachable portion which is detachably connected to the lamp receiving body 2 on the rear wall 19 of the hollow portion 9. For this purpose, the hollow portion 9 is connected by form fit and force fit, preferably detachably/releasably by means of a bayonet-type lock to the lamp receiving body 2. Thus, the completely assembled position of the surgical light 10 and, resp., of the handle device 1 is realized, as illustrated e.g. in FIG. 9.

In combination of FIGS. 17 and 18, another embodiment of the handle device 1 according to the invention is schematically represented, wherein said handle device 1 works and is designed according to the first embodiment. In contrast, here the external cover 35 of the acoustic sensor 29 is inserted in a frame formed by the electronic housing 33 and thus is held especially skillfully by form fit within the electronic housing 33. It is visible from FIG. 18 that in the housing 8 of the sensor module 6, viz. in the front wall 18 thereof, a recess 34 corresponding to the electronic housing 33 is formed into which the electronic housing 33 protrudes from the side of the external cover 35.

In connection with FIG. 10, a further embodiment of the handle device 1 according to the invention is disclosed, wherein primarily another voice control module 6 is evident in an alternative configuration. The voice control module 6 only consists of the afore-described disk-shaped hollow portion 9 in the form of an intermediate ring forming the housing 8. Here a handle receiving portion 11 in the form of a receiving pivot 12 is omitted. This embodiment realizes the fact that an existing handle device 1 is detachably connected directly to the housing 8. Consequently, it is possible also for this reason to provide a detachable voice control module 6. The design and functioning thereof corresponds to the voice control module 6 of the first embodiment.

In addition, in FIG. 14 another embodiment of the handle device 1 according to the invention is schematically represented, with the handle device 1 in turn being fastened already to the lamp receiving body 2. In this case, the handle device 1 substantially corresponds to the handle device 1 of the first embodiment. The surgical light 10, too, substantially corresponds to the surgical light 10 as described in connection with FIGS. 5, 6, 9 and 11 to 13. The individual lamps 30 of the surgical light 10 forming the lamp fields 31 are schematically shown as rectangles each producing plural light beams/light beam bundles so as to form a common light field 38/illumination field e.g. on an illumination plane 37 positioned in the wound field.

The central control unit of the surgical light 10 generally described before is also especially clearly schematically evident, wherein said control unit in this case is marked by the reference numeral 40. The control unit 40 is arranged in the lamp receiving body 2. The control unit 40 is electrically connected to each lamp field 31 via electric connecting lines 41. Inside the lamp fields 31 the connecting line 41 in turn is split in such way that each individual lamp 30 is electrically connected to the connecting line 41 by a secondary line.

Also, the voice control module 4 schematically shown here is in the form of a "stand-alone" module and is connected to the control unit 40 by means of data communication 42. The data communication 42 in this embodiment is implemented by a data communication line 43 shown by a broken line here, i.e. electrically/cable-bound. In a further embodiment, said data communication 42 is also in the form of a wireless communication.

In contrast to the first embodiment, the handle device 1 further comprises an image-recording device 34 including a camera, viz. a video camera for shooting the wound field/the illumination plane 37. The image-recording device 34 in addition includes sound recording means for recording a sound as well as a loudspeaker which are not shown here for the sake of clarity. The image-recording device 34 is arranged inside, i.e. radially inside the handle element 3. The image-recording device 34 further is integrated in the handle receiving portion 11/the receiving pivot 12. Accordingly, the video camera of the image-recording device 34 is oriented with its lens toward a side of the handle device 1 facing away from the lamp receiving body 2. To this end, the cover 16 is preferably omitted or is formed to be transparent to light which can be perceived by the video camera. Equally, in the image-recording device 34 within the handle device 1 a storage unit in the form of a memory card is integrated which is connected to the video camera and is configured for storing the data recorded by the video camera.

The image-recording device 34 in turn is electrically connected to the control unit 40 in the operating state according to FIG. 14 by another connecting line 41. The power supply of the image-recording device 34, of the voice recognition unit 15 and the computer unit 14 during operation is ensured by means of said connecting line 41. Current is also supplied to the distance sensors 7 by means of said connecting line 41 during operation.

In addition, the image-recording device 34 is electrically connected to the voice control module 4. This allows to directly actuate, viz. activate and deactivate, the image-recording device 34 by the voice control module 4. Thus, recording by the video camera can be started and/or stopped equally by means of voice input/voice command. Also, voice memo recording can be stored directly on the memory card by means of the sound recording means in this way. The data detected by the image-recording device 34 then are transmitted during operation by means of the data communication 42 to the control unit 40 and are forwarded or processed by the latter.

The connecting lines 41 and the data communication 42 are part of a cable-bus system, viz. a CAN bus system.

In FIGS. 18 and 19, a further embodiment of the handle device 1 according to the invention is shown, wherein said handle device 1 functions and is designed according to the embodiment of FIG. 14. In this case, especially the handle element 3 is designed to be thicker, however. This is due to the fact that in the handle element 3 a video camera forming the image-recording device 36 for recording the wound field is arranged. The outermost pane/the outermost glass of the lens of the image-recording device 36 is evident, with the light entrance axis thereof being formed concentrically with a through-hole 38. The image-recording device 36 is surrounded by the handle surface 5, but in the area of the cover 16 it is provided with the through-hole 38 through which the image-recording device 36 detects the outside of the handle device 1.

REFERENCE NUMERALS

1 Handle device
1' prior art handle device
2 lamp receiving body
3 handle element
4 exterior region
5 handle surface
6 voice control module/sensor module
7 distance sensor
8 housing
9 hollow portion
10 surgical light
11 handle receiving portion
12 receiving pivot
13 sleeve portion
14 computing unit
15 voice recognition unit
16 cover
17 broadening portion
18 front wall
19 rear wall
20 sidewall
21 printed circuit board
22 infrared transmitter
23 infrared receiver
24 active area
25 object
26 directional axis
27 receiving plane
28 cover area
29 acoustic sensor/microphone
30 individual lamp
31 lamp field
32 longitudinal axis 33 electronic housing
35 external cover
36 image-recording device
37 illumination plane
38 light field
39 light beam
40 control unit
41 connecting line
42 data communication
43 data communication line

The invention claimed is:

1. A handle device which is prepared for attachment to a receiving body of a surgical light, the handle device comprising a housing including a disk-shaped hollow portion with a front wall and a rear wall being distanced to the front wall via a side wall, a handle receiving portion being tightly connected to the front wall and forming a receiving pivot that extends with its longitudinal axis perpendicular to and away from the front wall, a handle element including a sleeve portion that forms a handle surface in an exterior region and is detachably arranged on the receiving pivot in such a way that a voice control module comprising the housing is detachably connected to the handle element, wherein inside the disk-shaped hollow portion of the housing an electronic housing is placed and inside this electronic housing at least one acoustic sensor and a loudspeaker as an acoustic output unit are enclosed.

2. The handle device according to claim 1, wherein the housing is transmissive to an acoustic signal to be detected by the at least one acoustic sensor in the area of the at least one acoustic sensor.

3. The handle device according to claim 1, wherein the handle element is connected to the voice control module by form fit and/or force fit in at least one operating state.

4. The handle device according to claim 1, wherein the voice control module includes a computer unit which is electrically connected to the at least one acoustic sensor and generates control signals for controlling the surgical light depending on the measuring data determined by means of the at least one acoustic sensor.

5. The handle device according to claim 1 wherein at least one distance sensor designed for detecting a position of an object is contained in the voice control module.

6. The handle device according to claim 4, wherein the at least one distance sensor is electronically connected to the computer unit.

7. The handle device according to claim 1, wherein the voice control module is connected to an image-recording device.

8. A surgical light comprising a handle device according to claim 1, wherein the handle device is at least partially detachably connected to a receiving body of the surgical light.

9. The surgical light according to claim 8, wherein the voice control module is detachably attached to the receiving body.

10. The surgical light according to claim 8, wherein a computer unit of the voice control module is wire-connected to a central control unit of the surgical light.

11. The surgical light according to claim 8, wherein a computer unit of the voice control module is connected to a central control unit of the surgical light by means of wireless data communication.

12. The handle device according to claim 1, wherein the loudspeaker is positioned directly behind a wipeable membrane.

* * * * *